United States Patent
Madry et al.

(10) Patent No.: US 9,017,073 B2
(45) Date of Patent: Apr. 28, 2015

(54) DISPOSABLE PROPHYLAXIS ANGLE WITH IMPROVED GEAR RETAINER

(71) Applicant: Young Dental Manufacturing I, LLC, Earth City, MO (US)

(72) Inventors: Roger Madry, Troy, MO (US); Steve Tripp, High Ridge, MO (US); Tom Richardson, Pacific, MO (US); Jim Curry, Fenton, MO (US)

(73) Assignee: Young Dental Manufacturing I, LLC, Chicago, IL (US)

( * ) Notice: Subject to any disclaimer, the term of this patent is extended or adjusted under 35 U.S.C. 154(b) by 93 days.

(21) Appl. No.: 13/682,862

(22) Filed: Nov. 21, 2012

(65) Prior Publication Data

US 2014/0141386 A1    May 22, 2014

(51) Int. Cl.
*A61C 3/06*    (2006.01)
*A61C 17/24*   (2006.01)
*A61C 1/12*    (2006.01)

(52) U.S. Cl.
CPC . *A61C 17/24* (2013.01); *A61C 1/12* (2013.01); *Y10T 29/49464* (2015.01)

(58) Field of Classification Search
CPC ............ A61C 3/02; A61C 3/03; A61C 17/24; A61C 1/12; Y10T 29/49464
USPC .......................... 433/103–129, 133
See application file for complete search history.

(56) References Cited

U.S. PATENT DOCUMENTS

| | | |
|---|---|---|
| 5,156,547 A | 10/1992 | Bailey |
| 5,423,679 A | 6/1995 | Bailey |
| 5,503,555 A | 4/1996 | Bailey |
| 5,642,995 A | 7/1997 | Bailey |
| 5,730,595 A * | 3/1998 | Bailey ............................ 433/125 |
| 5,749,728 A | 5/1998 | Bailey |
| 6,099,309 A * | 8/2000 | Cardarelli ...................... 433/125 |
| 6,203,322 B1 * | 3/2001 | Kraenzle ........................ 433/125 |
| 6,527,552 B2 | 3/2003 | Loddeke et al. |
| 7,255,559 B2 | 8/2007 | Shen et al. |
| 7,261,561 B2 | 8/2007 | Ruddle et al. |
| 7,762,813 B2 | 7/2010 | Seals et al. |
| 2005/0130100 A1 * | 6/2005 | Wade .............................. 433/125 |
| 2009/0035719 A1 | 2/2009 | Seals et al. |

OTHER PUBLICATIONS

International Search Report and Written Opinion for PCT/US2013/067015 dated Jan. 24, 2014.

* cited by examiner

*Primary Examiner* — Heidi M Eide
(74) *Attorney, Agent, or Firm* — McDermott Will & Emery LLP

(57) ABSTRACT

Disclosed are embodiments of a dental prophylaxis angle. One dental prophylaxis angle includes a body having a neck that defines a first axial bore and a head that defines a second axial bore, the first and second axial bores communicating at an intersection and being angularly-offset from each other, a drive gear rotatably mounted in the first axial bore and having a drive gear head and a locking flange axially-offset from the drive gear head, an annular locking groove being defined between the drive gear head and the locking flange, a driven gear rotatably mounted in the second axial bore and operatively coupled to the drive gear, and a gear retainer having an annular body configured to extend about an outer surface of the head, a heel extending from the annular body, an arm extending from the heel, and a wedge extending from the arm.

20 Claims, 4 Drawing Sheets

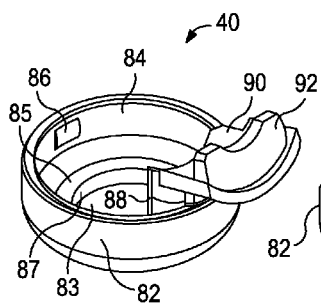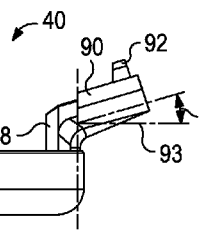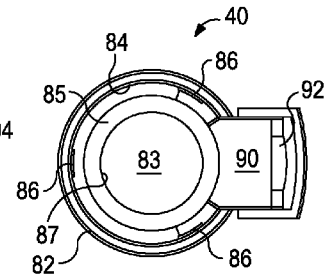
FIG. 4a   FIG. 4b   FIG. 4c
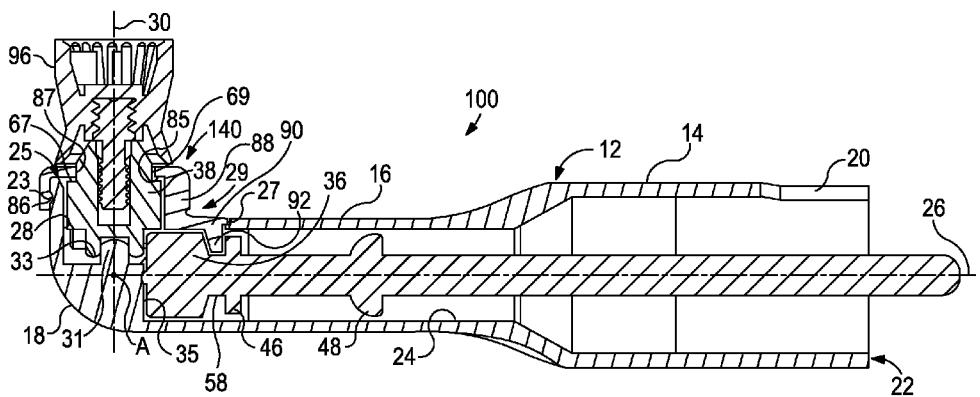
FIG. 5
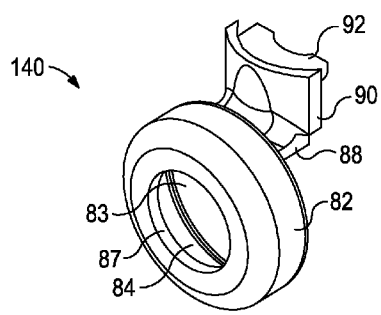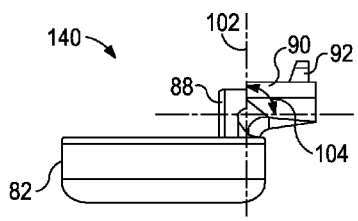
FIG. 6a   FIG. 6b

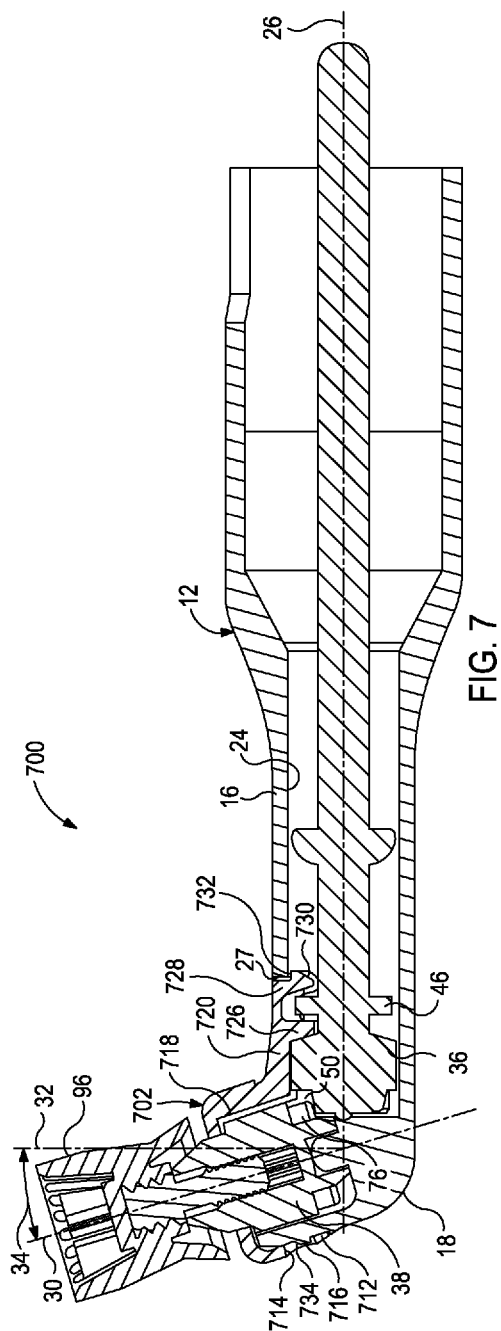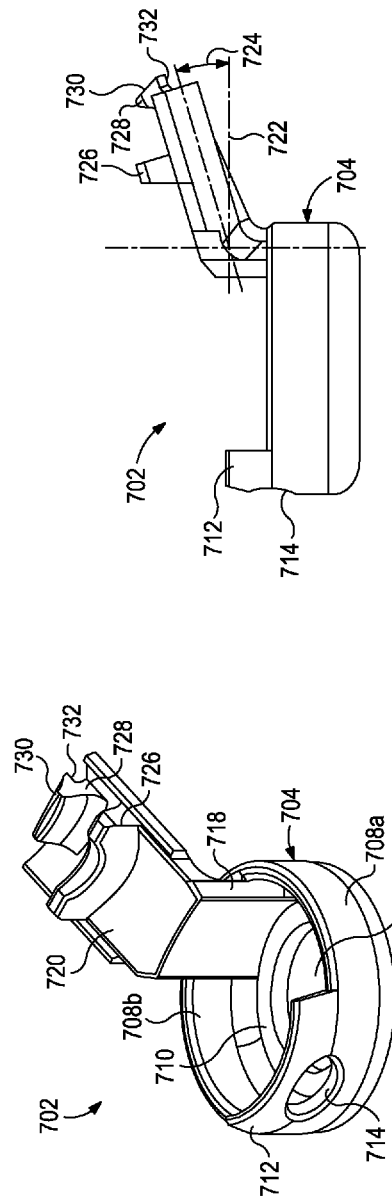

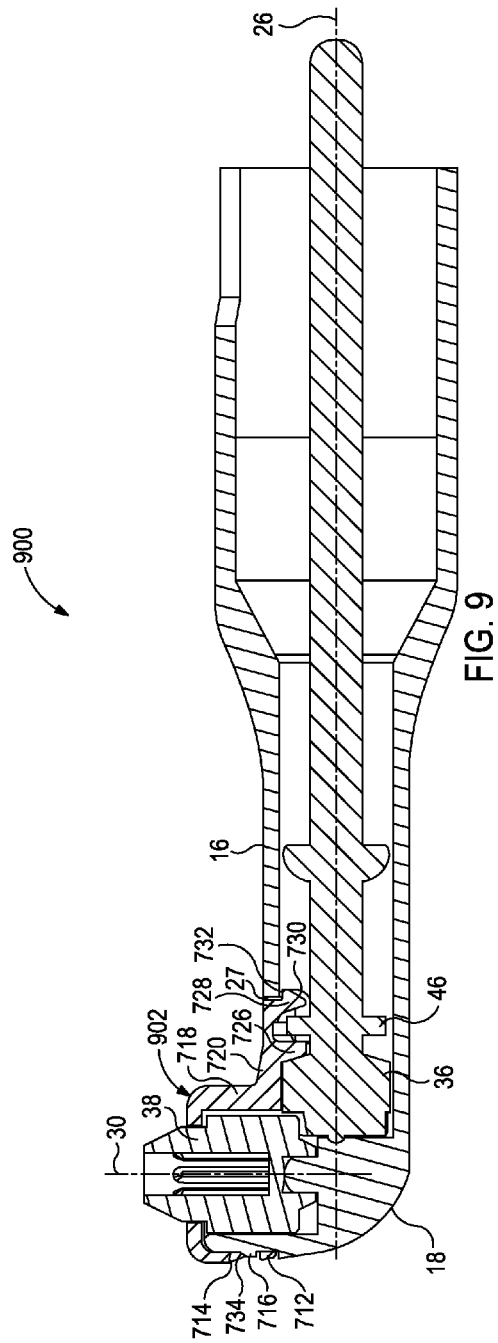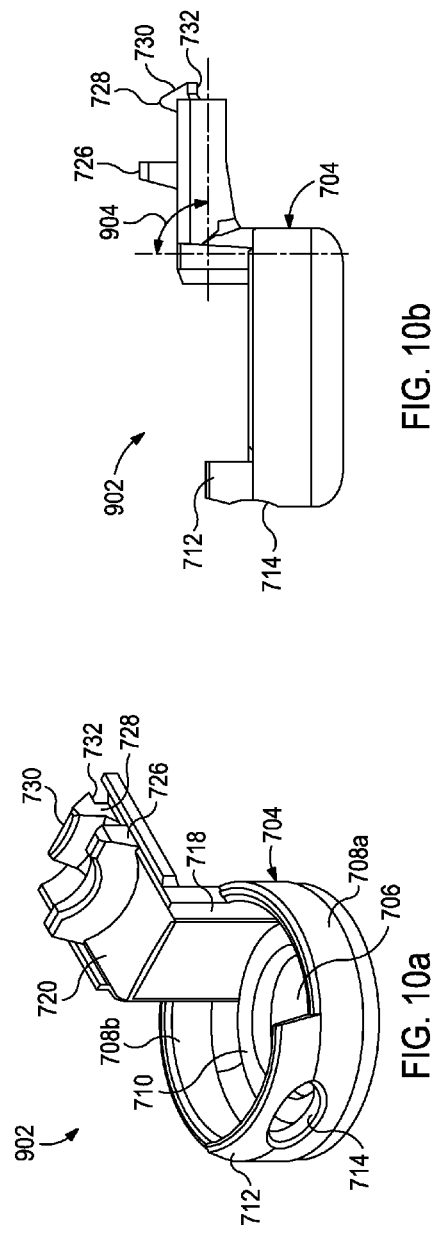
FIG. 9
FIG. 10a
FIG. 10b

DISPOSABLE PROPHYLAXIS ANGLE WITH IMPROVED GEAR RETAINER

FIELD OF THE INVENTION

The present technology generally relates to dental or prophylaxis angles and, more specifically, to disposable prophylaxis angles and methods of use.

BACKGROUND

Prophylaxis angles (aka "prophy" angles or dental angles) are used by dental personnel to clean and/or polish teeth. Prophy angles generally include a body having a head, where the head has a central axis angled relative to a central axis of the body. The structural angle between the two central axes is normally 90°. However, other types of prophy angles, known as contra-angles, include a head angled from the body at an angle greater than 90°. Typically, the head of a contra-angle may be angled between about 10° to about 30° greater than 90° from the axis of the body. Contra-angles can be used by dental personnel for reaching difficult spots within the mouth of a patient. Prophy angles will usually have a dental bit, such as a prophy cup, a brush, and/or a bur, coupled at the end of the head that allows the dentist to clean and polish a patient's teeth.

Drive and driven gears are arranged within the body of the prophy angle in a meshing relationship in order to rotate the dental bit. In some devices, a cap slips over the driven gear and attaches to the body in order to secure the gears within the body. A portion of the driven gear usually extends out of an opening in the cap and provides a location where the dental bit can be attached. Once entirely assembled, the prophy angle can be coupled to a handpiece, such as a Doriot-type handpiece. Specifically, the body is slipped over the nose of the handpiece which has a collet adapted to receive the shaft of the driving gear. The collet holds the drive shaft against axial movement and connects the shaft to a motor adapted to rotate the driving gear which, in turn, rotates the driven gear and the dental bit.

In the past, dentists used non-disposable, metal prophy angles. While sturdy, metal prophy angles required extensive care to ensure against transferring disease and germs from one patient to another. If the metal prophy angle is not properly sealed, bodily fluids from a patient, such as saliva and/or blood, can penetrate the prophy angle. Simply wiping down the metal prophy angle between uses is not adequate sterilization. Rather, to achieve proper sterilization, the metal prophy angles must be autoclaved after each use and periodically disassembled and thoroughly cleaned in order to remove contamination. Cleaning the metal prohpy angles also removes any grit which may have penetrated the housing which, if not properly removed, might interfere with the gears and thereby reduce the operating life of the metal prophy angle or otherwise make it difficult to operate. Metal prophy angles also require periodic lubrication to ensure that the gears run smoothly, quietly, and efficiently to reduce heat build-up. Thus, the care required for metal prophy angles is quite extensive.

Due to the extensive care required by non-disposable prophy angles, plastic disposable prophy angles are desired by dentists. Disposable prophy angles are much more sanitary than non-disposable ones, and therefore more useful in preventing cross-contamination between patients. Moreover, their disposable nature eliminates the need to thoroughly sanitize, clean, and lubricate them between each use. While various types and configurations of disposable prophy angles have been made, it nonetheless remains beneficial to find improved disposable prophy angles that offer advantages over prior models.

SUMMARY OF THE INVENTION

In some embodiments, a dental prophylaxis angle is disclosed and may include a body having a neck that defines a first axial bore and a head that defines a second axial bore, the first and second axial bores communicating at an intersection and being angularly-offset from each other, and the body defining an opening that spans contiguous portions of both the neck and the head. A drive gear may be rotatably mounted in the first axial bore and having a drive gear head and a locking flange axially-offset from the drive gear head, an annular locking groove being defined between the drive gear head and the locking flange. A driven gear may be rotatably mounted in the second axial bore and operatively coupled to the drive gear. A gear retainer may be included and have an annular body configured to extend about an outer surface of the head, a heel extending from the annular body, an arm extending from the heel, and a wedge extending from the arm, wherein the heel and the arm are cooperatively configured to cover the opening and the wedge is configured to be received in the annular locking groove.

In other embodiments, a method of assembling a prophylaxis angle is disclosed. The method may include inserting a drive gear into a first axial bore defined within a neck of an angle body, the drive gear having a drive gear head and a locking flange axially-offset from the drive gear head, and inserting a driven gear into a second axial bore defined within a head of the angle body, the first and second axial bores being angularly-offset from each other and communicating at an intersection in the angle body, the body defining an opening that spans contiguous portions of both the neck and the head. The method may also include operatively coupling the drive gear to the driven gear such that rotation of one rotates the other, and installing a gear retainer on the head, the gear retainer having an annular body that extends about an outer surface of the head, a heel extending from the annular body, an arm extending from the heel, and a wedge extending from the arm.

In yet other embodiments, a gear retainer for securing a drive gear and a driven gear within a prophylaxis angle housing may be disclosed. The gear retainer may include an annular body configured to extend about an outer surface of a head of the prophylaxis angle housing when installed, a heel extending from the annular body, an arm extending from the heel at an angle, and a wedge extending orthogonally from the arm.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present disclosure, and should not be viewed as exclusive embodiments. The subject matter disclosed is capable of considerable modification, alteration, and equivalents in form and function, as will occur to those skilled in the art and having the benefit of this disclosure. Moreover, while the subject technology is susceptible of many different embodiments, there is shown in the drawings and will herein be described in detail various embodiments of the disclosure with the understanding that the embodiments are to be considered an exemplification of the principles of the subject

FIGS. 4a-4c illustrate isometric, side, and interior views, respectively, of an exemplary gear retainer, according to one or more embodiments disclosed.

FIG. 5 illustrates another exemplary prophy angle, according to one or more embodiments disclosed.

FIGS. 6a and 6b illustrate isometric and side views of another exemplary gear retainer, according to one or more embodiments disclosed.

FIG. 7 illustrates another exemplary prophy angle, according to one or more embodiments disclosed.

FIGS. 8a and 8b illustrate isometric and side views of another exemplary gear retainer, according to one or more embodiments disclosed.

FIG. 9 illustrates another exemplary prophy angle, according to one or more embodiments disclosed.

FIGS. 10a and 10b illustrate isometric and side views of another exemplary gear retainer, according to one or more embodiments disclosed.

DETAILED DESCRIPTION

Figure 1:
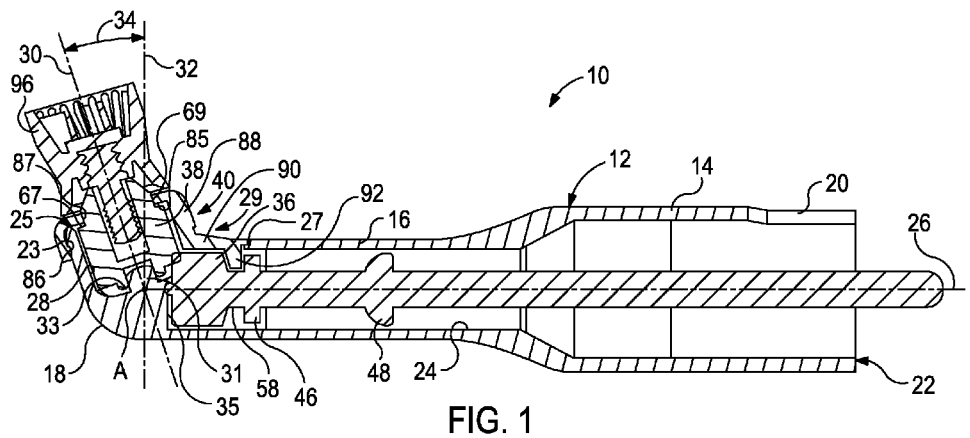
FIG. 1 illustrates an exemplary prophy angle, according to one or more embodiments disclosed.

While the present invention is susceptible of many different embodiments, there is shown in the drawings and will herein be described in detail one or more exemplary embodiments of the invention with the understanding that the present disclosure is to be considered an exemplification of the principles of the invention and is not intended to limit the broad aspect of the invention to the embodiments illustrated.

Referring to FIG. 1, illustrated is an exemplary prophylaxis angle ("prophy" angle) 10, according to one or more embodiments disclosed. The prophy angle 10 includes a body 12 having a sleeve 14, a neck 16, and a head 18. In one embodiment, the sleeve 14, neck 16, and head 18 may be formed as a single, integral piece. In other embodiments, however, the sleeve 14, neck 16, and head 18 may be individual components coupled together by various means, including, but not limited to, mechanical fasteners, structural threading, adhesives, ultrasonic welding, combinations thereof, or the like. As illustrated, the sleeve 14 may be formed as an elongate cylinder, having a generally circular cross-section, but may equally be formed using other hollow, accommodating shapes, without departing from the scope of the disclosure. A slot 20 may be defined at the distal end 22 of the sleeve 14 and configured to receive a positioning pin or finger from a handpiece (not shown), such as a standard Doriot-type handpiece. In one embodiment, the slot 20 is longer than necessary to accommodate the positioning pin from the handpiece, and the thinness of the walls of the sleeve 14 permits the sleeve 14 to expand slightly when it is forced onto the corresponding handpiece for operation.

The proximal end of the sleeve 14 tapers to the neck 16, which exhibits a smaller outside and inside diameter than the sleeve 14 but is nonetheless coaxial with the sleeve 14. The sleeve 14 and the neck 16 cooperatively define a first axial bore 24 having a first central axis 26. The head 18 is generally formed as a cylinder extending from the neck 16 and defining a second axial bore 28 that has a second central axis 30. The first and second axial bores 24, 28 are in communication with each other at an intersection 29 of the neck 16 and the head 18.

In one embodiment, an annular or generally arcuate groove 23 is defined about at least a portion of the distal end 25 of the head 18. An opening 27 may be defined in the neck 16 behind the head 18, and may span contiguous portions of both the neck 16 and the head 18. In one embodiment, the opening 27 may be generally rectangular in shape. In other embodiments, however, the opening 27 may take the form of other shapes without departing from the scope of the disclosure.

The interior of the head 18 may further define an axial protrusion 31, an annular channel 33, and an interior biasing surface 35. The axial protrusion 31 extends axially into the second axial bore 28 and provides a mounting location for a driven gear 38, as will be described below. The annular channel 33 may be defined in the head 18 about the base of the axial protrusion 31, and may also facilitate a portion of the mounting location for the driven gear 38. The interior biasing surface 35 is generally orthogonal to the first central axis and is exposed to the first axial bore 24.

As illustrated, the head 18 may be disposed at an angle with respect to the neck 16, with the first central axis 26 intersecting the second central axis 30 at point A. Other prophy angles, such as the prophy angle 100 described below with reference to FIG. 5, have the second central axis 30 disposed at a right angle 32 (i.e., 90° from the first central axis 26) with respect to first central axis 26. The prophy angle 10 illustrated in FIG. 1 may be characterized as a contra-angle, where the second central axis 30 is angularly-offset from the right angle 32 by a first angle 34. In one or more embodiments, the first angle 34 ranges between about 10° to about 30°. In at least one embodiment, however, the first angle 34 may be about 15° to about 22°.

Figures 2A, 2B:
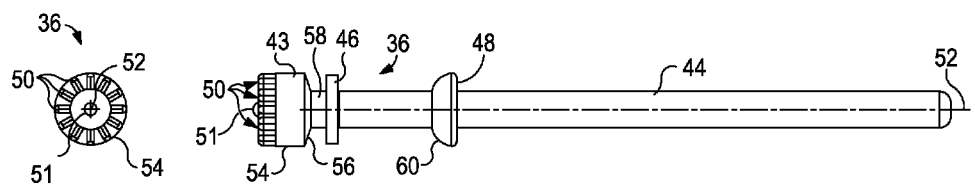
FIGS. 2a and 2b illustrate front and side views, respectively, of an exemplary drive gear, according to one or more embodiments disclosed.

The prophy angle 10 further includes a drive gear 36, a driven gear 38, and a gear retainer 40 to secure the drive and driven gears 36, 38 within the body 12. Referring to FIGS. 2a and 2b, illustrated are front and side views, respectively, of the drive gear 36, according to one or more embodiments. The drive gear 36 includes a drive gear head 43, an elongate, rotatable shaft 44 extending from the drive gear head 43, a locking flange 46, an intermediate flange 48, and a plurality of angularly-spaced driving teeth 50 extending axially from the proximal end of the drive gear head 43. The driving teeth 50 extend about a rotational axis 52 of the drive gear 36. As can be appreciated, the rotational axis 52 of the drive gear 36 may be substantially co-axial with the first central axis 26 (FIG. 1) when the prophy angle 10 is fully assembled. In one embodiment, a drive gear protrusion 51 may be defined on the end of the shaft 44 and extend axially from the driving teeth 50 a short distance.

The drive gear head 43 includes a drive bearing surface 54 and a tapered trailing edge 56. In one embodiment, the drive bearing surface 54 is the outer circumferential surface of the drive gear head 43 and extends axially from the plurality of driving teeth 50. The tapered trailing edge 56 provides a structural transition from the drive bearing surface 54 to the shaft 44. The locking flange 46 is axially-spaced from the drive gear head 43 and, in particular, from the tapered trailing edge 56, thereby defining an annular locking groove 58 therebetween. In one embodiment, the locking groove 58 may have an outside diameter that is substantially the same as the diameter of the shaft 44. In other embodiments, the outside diameter of the locking groove 58 may be more or less than the outside diameter of the shaft 44, without departing from the scope of the disclosure. In some embodiments, the locking groove 58 may be configured to receive a portion of the gear retainer 40 in order to secure the drive gear 36 within the body 12 (FIG. 1), as will be described in more detail below.

The intermediate flange 48 may be axially-spaced from the locking flange 46 along the length of the shaft 44. In one embodiment, the intermediate flange 48 forms an integral part of the shaft 44 and is molded or otherwise constructed therewith as a single structural element. In other embodiments, however, the intermediate flange 48 is coupled to the shaft 44 using various means known in the art, such as, but not limited to, mechanically-fastening, ultrasound welding, adhesives, combinations thereof, or the like. In one embodiment, the intermediate flange 48 has a tapered leading edge 60 to allow for easier assembly of the prophy angle 10.

Both the drive bearing surface 54 and the intermediate flange 48 may have respective outside diameters that are larger than that of the shaft 44 but slightly less than the inside diameter of the first axial bore 24 defined in the neck 16 (FIG. 1). Accordingly, during operation the drive bearing surface 54 and the intermediate flange 48 may each be configured to bias the inside surface of the first axial bore 24 or otherwise help maintain the drive gear 36 substantially centered therein. In one or more embodiments, the locking flange 46 may also have a similarly-sized outside diameter so as to help maintain the drive gear 36 substantially centered within the first axial bore 24.

Figures 3A, 3B, 3C:
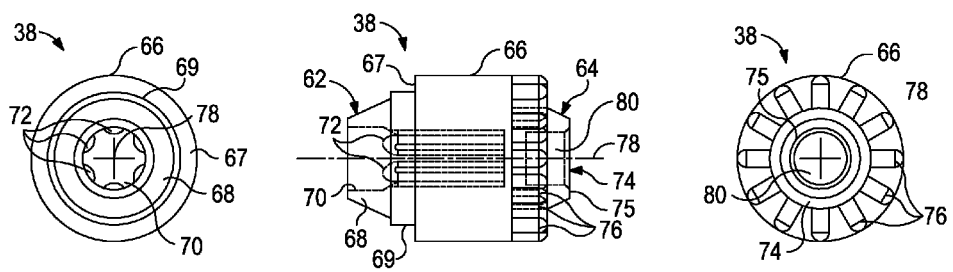
FIGS. 3a-3c illustrate front, side, and end views, respectively, of an exemplary driven gear, according to one or more embodiments disclosed.

Referring now to FIGS. 3a, 3b, and 3c, illustrated are front, side, and end views, respectively, of the driven gear 38, according to one or more embodiments disclosed. The driven gear 38 may be a generally-cylindrical structure having a rotational axis 78 that may be substantially co-axial with the second central axis 30 (FIG. 1) when the driven gear 38 is fully assembled within the prophy angle 10. The driven gear 38 includes a first end 62, a second end 64, and a driven bearing surface 66 extending between the first and second ends 62, 64. The first end 62 may include a boss 68 that defines a bit cavity 70 therein. The bit cavity 70 may extend axially into the driven gear 38 and define a plurality of axially-extending splines 72 therein. The splines 72 may be configured to engage or otherwise secure a dental bit to the driven gear 38, as will be described below. In other embodiments, the splines 72 may be substituted for other engagement means such as, screw threadings, without departing from the scope of the disclosure.

The boss 68 may be a tapered, annular structure, but in other embodiments, the boss 68 may be a substantially-cylindrical structure, without departing from the scope of the disclosure. The first end 62 may further define a shoulder 67 adjacent the driven bearing surface 66 and substantially orthogonal to the rotational axis 78. The shoulder 67 may provide a structural transition from the driven bearing surface 66 to a radial surface 69 substantially parallel to the rotational axis 78, but orthogonal to the shoulder 67. The shoulder 67 and the radial surface 69 may each be configured to bias corresponding portions of the gear retainer 40 in order to maintain the driven gear 38 in its assembled configuration and centered within the second axial bore 28 (FIG. 1) during operation.

The second end 64 of the driven gear 38 may define a mounting pedestal 74 and a plurality of angularly-spaced driven teeth 76. The driven teeth 76 may extend about the rotational axis 78 and also about the outer circumferential surface of the mounting pedestal 74. The driven teeth 76 may be configured to engage the drive teeth 50 (FIGS. 2a and 2b) in a generally meshing relationship. In one embodiment, the drive and driven teeth 50, 76 are characterized as corresponding spur gears with straight teeth 50, 76 parallel to their respective axes of rotation 52, 78. In other embodiments, however, the drive and driven teeth 50, 76 may be corresponding bevel gears, where the axes of rotation 52, 78 intersect but the gears 36, 38 are conically-shaped such that the axes 52, 78 are not orthogonal, but angularly-offset.

A mounting cavity 80 may be defined within the mounting pedestal 74. The mounting cavity 80 may be configured to receive the axial protrusion 31 (FIG. 1) defined in the head 18 when the driven gear 38 is inserted into the second axial bore 28, thereby mounting the driven gear 38 for rotation therein. In one embodiment, the mounting pedestal 74 is a tapered, annular structure. In other embodiments, however, the mounting pedestal 74 may be substantially cylindrical. In either case, a mounting surface 75 of the mounting pedestal 74 may be received within or otherwise come into close proximity with the annular channel 33 (FIG. 1) defined in the head 18.

The driven bearing surface 66 may have an outside diameter that is slightly less than that of the inside diameter of the second axial bore 28 (FIG. 1). Accordingly, the driven bearing surface 66 may be configured to bias the inner surface of the second axial bore 28 and thereby maintain the driven gear 38 substantially centered therein during use.

Referring now to FIGS. 4a, 4b, and 4c, illustrated are isometric, side, and interior views, respectively, of an exemplary gear retainer 40, according to one or more embodiments disclosed. The gear retainer 40 may have a generally annular body 82 defining a central opening 83 and an inner circumferential surface 84 that transitions orthogonally into a generally planar, first retaining surface 85. The central opening 83 provides a second retaining surface 87, substantially orthogonal to the first retaining surface 85. The first and second retaining surfaces 85, 87 may be configured to engage or otherwise bias the shoulder 67 and the radial surface 69, respectively, of the driven gear 38 (FIGS. 3a and 3b) when the prophy angle 10 is in its assembled configuration.

One or more retainer protrusions 86 may be arranged or otherwise formed about the inner circumferential surface 84 of the gear retainer 40. The retainer protrusions 86 may be equidistantly-spaced about the inner circumferential surface 84, or they may be randomly-spaced, without departing from the scope of the disclosure. The retainer protrusions 86 may be configured to be received into (e.g., snapped into) and/or generally mate with the arcuate groove 23 (FIG. 1) defined about the distal end 25 of the head 18. In at least one embodiment, the retainer protrusions 86 are omitted from the gear retainer 40, and the gear retainer 40 is otherwise secured to the head 18 by other means of attachment such as, but not limited to, ultrasonic welding, mechanical attachments, adhesives, combinations thereof, and the like.

The gear retainer 40 may also include an arcuate heel 88 that extends from the annular body 82, an arcuate arm 90 that extends from the heel 88, and an arcuate wedge 92 that extends from the arm 90. As illustrated in FIG. 4b, the heel 88 extends substantially perpendicular from the annular body 92, forming a right angle 93 therebetween. The arm 90 extends from the heel 88 at an angle 94 offset from the right angle 93. The angle 94 is configured to generally correspond to the first angle 34 (FIG. 1) and thereby accommodate the angular offset between the first and second central axes 28, 30 (FIG. 1). Accordingly, the angular disposition between the heel 88 and the arm 90 allows the gear retainer 40 to properly cover the opening 27 (FIG. 1) that extends across portions of both the neck 16 and the head 18. Specifically, the arcuate heel 88 may cover the opening 27 spanning the portion of the head 18, and the arcuate arm 90 may cover the opening 27 spanning the portion of the neck 16.

Referring again to FIG. 1, with continued reference to FIGS. 2a-b, 3a-c, and 4a-c, the prophy angle 10 may be assembled by inserting the drive gear 36 axially into the first axial bore 24 through the opening at the distal end 22 of the body 12. The drive gear 36 is advanced until the drive gear protrusion 51 (FIG. 2) comes into contact with the interior biasing surface 35 of the head 18, or otherwise comes substantially close thereto. As can be appreciated, the drive gear protrusion 51 may serve to axially-offset the drive gear 36 from the head 18 so that the driving teeth 50 may rotate unobstructed from the head 18 during operation.

The driven gear 38 may then be inserted axially into the second axial bore 28, leading with its second end 64 (FIGS. 3b and 3c). The driven gear 38 is advanced until the axial protrusion 31 defined in the head 18 is received into the mounting cavity 80 defined in the mounting pedestal 74 (FIGS. 3b and 3c) and the mounting surface 75 of the mounting pedestal 74 is received into the annular channel 33. Inserting the driven gear 38 into the second axial bore 28 also places the driven teeth 76 in meshing engagement with the driving teeth 50 (FIGS. 2a-b), such that rotation of one causes rotation of the other.

Once the teeth 50, 76 are engaged for mutual operation, the gear retainer 40 may be installed on the head 18 to prevent the drive and driven gears 36, 38 from being removed from the body 12. To install the gear retainer 40, the central opening 83 (FIGS. 4a and 4c) is aligned with the first end 62 (FIG. 3b) of the driven gear 36 and the boss 68 (FIGS. 3a and 3b) is extended therethrough. The inner circumferential surface 84 (FIGS. 4a and 4c) of the gear retainer 40 has a slightly larger diameter than the outer circumferential surface of the head 18 such that the inner circumferential surface 84 can be extended over the outer circumferential surface of the head 18. As the gear retainer 40 is advanced onto the head 18, the radial disposition of the heel 88 and arm 90 (FIGS. 4a-4c) is adjusted so as to generally align with the opening 27. In one embodiment, the gear retainer 40 is advanced until the retainer protrusion(s) 86 (FIGS. 4a and 4c) snaps into the arcuate groove 23 defined about the distal end 25 of the head 18. In other embodiments, the gear retainer 40 may be formed such that it can be attached to the head 18 in other ways, such as via a threaded screw connection or adhesives. Once properly coupled, the gear retainer 40 may be ultrasonically-welded to the head 18 such that separation of the two components is prevented.

In this coupled and assembled configuration, the first retaining surface 85 (FIGS. 4a and 4c) of the gear retainer 40 engages or is otherwise substantially adjacent to the shoulder 67 of the driven gear 38 (FIGS. 3a and 3b). As illustrated in FIG. 1, the first retaining surface 85 also engages or is otherwise substantially adjacent to the distal end 25 of the head 18. The second retaining surface 87 (FIGS. 4a and 4C) of the gear retainer 40 engages or is otherwise substantially adjacent to the radial surface 69 of the driven gear 38 (FIGS. 3a and 3b). Moreover, the arcuate wedge 92 (FIGS. 4a-4c) is disposed or otherwise received within the locking groove 58 (FIG. 2b) to lock the drive gear 36 within the body 12 and prevent its axial displacement. By biasing against the tapered trailing edge 56 (FIG. 2b) on one side and against the axial face of the locking flange 46 (FIG. 2b) on the other side, the wedge 92 maintains the drive gear 36 in a position that allows for a proper meshing relationship between the drive and driven teeth 50, 76. Accordingly, the wedge 92 prevents the drive gear 36 from becoming displaced within the body 12 due to the rotation of the shaft 44. It will be appreciated that the tapered trailing edge 56 may facilitate easier installation of the wedge 92 within the locking groove 58.

During operation of the prophy angle 10, when the drive and driven gears 36, 38 are mutually rotating, the arcuate inner surfaces of the heel 88, the arm 90, and the wedge 92 may be configured to help maintain the drive and driven gears 36, 38 in co-axial relation with the first and second central axes 26, 30, respectively. Specifically, the arcuate inner surface of the heel 88 may be arranged adjacent to or otherwise in communication with the driven bearing surface 66 of the driven gear 38 (FIG. 3b); the arcuate inner surface of the arm 90 may be arranged adjacent to or otherwise in communication with the drive bearing surface 54 of the drive gear 36 (FIG. 2b); and the arcuate inner surface of the wedge 92 may be arranged adjacent to or otherwise in communication with the outer circumferential surface of the locking groove 58 of the drive gear 36 (FIG. 2b).

Still referring to FIG. 1, a dental bit 96 may be attached to the driven gear 38 via the bit cavity 70. In one embodiment, the dental bit 96 is screwed into the driven gear 38. In other embodiments, however, other means of attachment may be utilized, without departing from the scope of the disclosure. The dental bit 96 is used to clean or polish a patient's teeth. In addition to the dental bit 96, other dental instruments can be attached to the drive gear 38 as is well-known to those skilled in the art.

Referring now to FIG. 5, illustrated is another exemplary prophy angle 100 according to one or more embodiments of the disclosure. The prophy angle 100 may be substantially similar to the prophy angle 10 described above and therefore may be best understood with reference thereto, where like numerals correspond to like elements that will not be described again in detail. Unlike the prophy angle 10 described above, the first and second central axes 26, 30 of the prophy angle 100 may be arranged substantially perpendicular to each other, such that the head 18 is disposed at a right angle to the neck 16.

Referring to FIGS. 6a and 6b, illustrated are isometric and side views, respectively, of an exemplary gear retainer 140, according to one or more embodiments disclosed. The gear retainer 140 may be substantially similar to the gear retainer 40 described above and therefore may be best understood with reference to FIGS. 1 and 4a-4c, where like numerals correspond to like components that will not be described again. Similar to the gear retainer 40 described above, the arcuate heel 88 of the gear retainer 140 extends substantially perpendicular 102 from the annular body 82. Unlike the gear retainer 40, however, the arcuate arm 90 extends from the heel 88 at a generally orthogonal angle 104 with respect to the heel 88. The angle 104 corresponds to the angular offset between the first central axis 26 and the second central axis 30 (FIG. 5). Accordingly, since the first and second central axes 26, 30 in the prophy angle 100 are substantially perpendicular, the angle 104 between the heel 88 and the arm 90 will correspondingly be about 90°.

When properly installed, the heel 88 and the arm 90 of the gear retainer 140 cover the opening 27 (FIG. 5) that extends across portions of both the neck 16 and the head 18. Specifically, the arcuate heel 88 covers the opening 27 spanning the portion of the head 18, and the arcuate arm 90 covers the opening 27 spanning the portion of the neck 16. Moreover, the wedge 92 is received in the locking groove 58 defined between the trailing edge 56 of the drive gear 36 and the locking flange 46 (see FIG. 2b) and thereby locks the drive gear 36 within the body 12.

Referring now to FIG. 7, illustrated is another exemplary prophy angle 700, according to one or more embodiments. The prophy angle 700 may be substantially similar to the prophy angle 10 of FIG. 1 and therefore may be best understood with reference thereto, where like numerals will correspond to like elements not described again in detail. As illustrated, the drive gear 36 and driven gear 38 are arranged within the first and second axial bores 24, 28, respectively, as generally described above. The drive gear 36 and driven gear 38 are installed such that the driving and driven teeth 50, 76 are arranged in meshing engagement such that rotation of one causes rotation of the other. Once the teeth 50, 76 are engaged for mutual operation, a gear retainer 702 may be installed on the head 18 to prevent the drive and driven gears 36, 38 from accidentally being removed from the body 12.

Referring to FIGS. 8a and 8b, with continued reference to FIG. 7, illustrated are isometric and side views, respectively, of the gear retainer 702, according to one or more embodiments disclosed. The gear retainer 702 may be substantially similar to the gear retainer 40 of FIGS. 4a-4c and therefore may be best understood with reference thereto. As illustrated, the gear retainer 702 may have a body 704 that defines a central aperture 714 configured to receive a portion of the driven gear 38 when properly installed on the head 18 of the prophy angle 700. The body 704 may define an outer circumferential surface 708a and an inner circumferential surface 708b, and the inner circumferential surface 708b may transition orthogonally into a retaining surface 710 similar to the retaining surface 85 of FIGS. 4a-4c.

The gear retainer 702 may also include an arcuate flange 712 that extends from or otherwise forms part of the body 704 such that the inner circumferential surface 708b may extend into or otherwise merge with the inner surface of the arcuate flange 712. An aperture 714 may be defined in the body 704. In some embodiments, the aperture 714 may be defined entirely by or within the arcuate flange 704. In other embodiments, the aperture 714 may be defined entirely by or within the body 704. In yet other embodiments, the aperture 714 may be defined by a combination of both the arcuate flange 704 and the body 704, without departing from the scope of the disclosure. In operation, the aperture 714 may be configured to receive at least one protrusion 716 (FIG. 7) defined on the outer surface of the head 18 and thereby at least partially secure the gear retainer 702 to the body 12. Those skilled in the art will readily recognize that more than one aperture 714 may be defined in the body 704 and configured to receive a corresponding more than one protrusion 716 defined on the outer surface of the head 18, without departing from the scope of the disclosure.

Similar to the gear retainer 40 of FIGS. 4a-4c, the gear retainer 702 may also include an arcuate heel 718 that extends from the body 704 and an arcuate arm 720 that extends from the heel 718. As illustrated in FIG. 8b, the heel 718 extends substantially perpendicular from the body 704, thereby forming a right angle 722 therebetween, and the arm 720 extends from the heel 718 at an angle 724 offset from the right angle 722. The angle 724 may be configured to generally correspond with the first angle 34 (FIG. 7) and thereby accommodate the angular offset between the first and second central axes 28, 30. Accordingly, the angular disposition between the heel 718 and the arm 720 allows the gear retainer 700 to properly occlude the opening 27 (FIG. 7) defined across portions of both the neck 16 and the head 18 of the prophy angle 700. Specifically, the arcuate heel 718 may be configured to cover the opening 27 spanning the portion of the head 18, and the arcuate arm 720 may be configured to cover the opening 27 spanning the portion of the neck 16.

The gear retainer 702 may further include an arcuate wedge 726 and a locking mechanism 728 that extend orthogonally from the arm 720. As illustrated, the locking mechanism 728 may be offset a short distance from the arcuate wedge 726 on the arm 720. The locking mechanism 728 may include or otherwise define a beveled surface 730 and a locking surface 732.

Referring again to FIG. 7, to install the gear retainer 702 on the prophy angle 700, and thereby secure the drive and driven gears 36, 38 within the body 12, the gear retainer 702 may be extended over the head 18 such that the central opening 706 (FIGS. 8a and 8b) is aligned with and receives the driven gear 36 therethrough. The gear retainer 702 may be advanced until the aperture 714 defined in the body 704 receives the protrusion 716 defined on the head 18. In at least one embodiment, the protrusion 716 may define or otherwise provide a beveled surface 734 configured to engage and cause the arcuate flange 712 to flex until the protrusion 716 is received within the aperture 714 and the arcuate flange 712 is able to snap into place.

As the gear retainer 702 is advanced onto the head 18, the radial disposition of the heel 718 and the arm 720 may concurrently be adjusted so as to generally align with the corresponding portions of the opening 27. Once aligned with the opening 27, the arcuate wedge 726 and the locking mechanism 728 may be configured to receive the locking flange 46 therebetween as the arm 720 is secured into the opening 27, and thereby lock the drive gear 36 within the body 12 and prevent its axial displacement. The beveled surface 730 of the locking mechanism 728 may be configured to engage the neck 16 at the opening 27 and cause the locking mechanism 728 to flex and snap into place. Once snapped into place at the opening 27, the locking surface 732 may be configured to engage the inner surface of the first axial bore 24. Accordingly, the locking mechanism 728 and the arcuate flange 712 may cooperatively secure the gear retainer 702 to the prophy angle 700. In some embodiments, once properly secured to the prophy angle 700, the gear retainer 702 may be ultrasonically-welded to the head 18 such that separation of the two components is substantially prevented.

Referring now to FIG. 9, illustrated is another exemplary prophy angle 900 according to one or more embodiments of the disclosure. The prophy angle 900 may be substantially similar to the prophy angle 700 of FIG. 7 and therefore may be best understood with reference thereto, where like numerals will correspond to like elements not described again in detail. Unlike the prophy angle 700 described above, the first and second central axes 26, 30 of the prophy angle 900 may be arranged substantially perpendicular to each other, such that the head 18 is disposed at a right angle to the neck 16.

Referring to FIGS. 10a and 10b, illustrated are isometric and side views, respectively, of an exemplary gear retainer 902, according to one or more embodiments. The gear retainer 902 may be substantially similar to the gear retainer 702 of FIG. 7 and therefore may be best understood with reference thereto. Similar to the gear retainer 702 described above, the arcuate heel 718 of the gear retainer 902 extends substantially perpendicular from the body 704. Unlike the gear retainer 702, however, the arcuate arm 720 may extend from the heel 718 at a generally orthogonal angle 904 with respect to the heel 718. The angle 904 corresponds to the angular offset between the first central axis 26 and the second central axis 30 (FIG. 9). Accordingly, since the first and second central axes 26, 30 in the prophy angle 900 are substantially perpendicular, the angle 904 between the heel 718 and the arm 720 will correspondingly be about 90°. Installing the gear retainer 902 on the prophy angle 900 may be accomplished in a manner that is substantially similar to how the gear retainer 702 of FIG. 7 is installed, and therefore will not be described again in detail.

Once the prophy angles 10, 100, 700, 900 are assembled, they can be used by a hygienist or other dental professional to clean or polish teeth. The shaft 44 (FIG. 2b) of the drive gear 36 extends through the open distal end 22 of the body 12 so that it can be attached to a dental handpiece (not shown). In use, the dental handpiece provides rotary motion to the shaft 44, and rotation of the shaft 44 rotates the drive gear 36. Due to the meshing configuration between the drive gear 36 and the driven gear 38, rotation of the drive gear 36 causes rotation of the driven gear 38 which, in turn, rotates the dental bit 96. The compact design of the prophy angles 10, 100, 700, 900 provide increased visibility and maneuverability within a patient's mouth. When the hygienist is finished, the prophy angle 10, 100, 700, 900 may be disengaged from the dental handpiece and properly disposed of.

In one or more embodiments, some or all of the various components of the prophy angles 10, 100, 700, 900 described above may be made of plastic and manufactured, for example, by injection molding techniques. This provides for an inexpensive, disposable dental hand tool. As discussed earlier, disposable prophy angles are beneficial because they eliminate the need to sterilize the prophy angle between each patient. Thus, there is no risk of cross-contaminating patients. Moreover, the prophy angles 10, 100 generally described herein may exhibit a reduced overall size when compared to previous models. For example, the design of the disclosed prophy angles 10, 100 may allow for a significant reduction in the diameter and length of the body 12, especially the respective diameters and lengths of the neck 16 and the head 18. Those skilled in the art will readily appreciate that this reduces the overall surface area of the prophy angles 10, 100, thereby allowing the hygienist greater visibility of the teeth/mouth area as well as increase maneuverability while still providing the same cleaning method.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A dental prophylaxis angle, comprising:
   a body having a neck that defines a first axial bore and a head that defines a second axial bore, the first and second axial bores communicating at an intersection and being angularly-offset from each other, and the body defining an opening that spans contiguous portions of both the neck and the head;
   a drive gear rotatably mounted in the first axial bore and having a drive gear head and a locking flange axially-offset from the drive gear head, an annular locking groove being defined between the drive gear head and the locking flange;
   a driven gear rotatably mounted in the second axial bore and operatively coupled to the drive gear; and
   a gear retainer having an annular body that defines an inner circumferential surface of the gear retainer configured to extend about an outer circumferential surface of the head, a heel extending from the annular body, an arm extending from the heel, and a wedge extending from the arm, wherein the heel and the arm are cooperatively configured to cover the opening and the wedge is configured to be received in the annular locking groove.

2. The dental prophylaxis angle of claim 1, further comprising:
   at least one protrusion defined on the outer circumferential surface of the head; and
   a flange extending from the annular body and at least partially defining an aperture configured to receive the at least one protrusion when the gear retainer is installed on the head.

3. The dental prophylaxis angle of claim 2, wherein the at least one protrusion provides a beveled surface configured to engage and cause the flange to flex such that the at least one protrusion is able to be received within the aperture.

4. The dental prophylaxis angle of claim 1, wherein the gear retainer further comprises a locking mechanism offset from the wedge and also extending from the arm, wherein the wedge and the locking mechanism are configured to receive the locking flange therebetween and thereby secure the drive gear against axial displacement.

5. The dental prophylaxis angle of claim 4, wherein the arm extends from the heel at an angle corresponding to the angular-offset between the first and second axial bores.

6. The dental prophylaxis angle of claim 4, wherein the locking mechanism further comprises:
   a beveled surface configured to engage the neck at the opening and cause the locking mechanism to flex and snap into place at the opening; and
   a locking surface configured to engage an inner surface of the first axial bore, thereby preventing the gear retainer from removal from the opening.

7. The dental prophylaxis angle of claim 1, wherein the gear retainer is ultrasonically-welded to the head.

8. The dental prophylaxis angle of claim 1, further comprising:
   an arcuate groove defined about at least a portion of the outer circumferential surface of the head; and
   one or more retainer protrusions defined on the inner circumferential surface of the gear retainer, the one or more retainer protrusions being configured to be received into the arcuate groove to secure the gear retainer to the head.

9. A method of assembling a prophylaxis angle, comprising
    inserting a drive gear into a first axial bore defined within a neck of an angle body, the drive gear having a drive gear head and a locking flange axially-offset from the drive gear head;
    inserting a driven gear into a second axial bore defined within a head of the angle body, the first and second axial bores being angularly-offset from each other and communicating at an intersection in the angle body, the body defining an opening that spans contiguous portions of both the neck and the head; operatively coupling the drive gear to the driven gear such that rotation of one rotates the other; and
    installing a gear retainer on the head, the gear retainer having an annular body that defines an inner circumferential surface of the gear retainer and extends about an outer circumferential surface of the head, a heel extending from the annular body, an arm extending from the heel, and a wedge extending from the arm.

10. The method of claim 9, wherein installing the gear retainer on the head further comprises receiving at least one protrusion defined on the outer circumferential surface of the head into an aperture at least partially defined in a flange extending from the annular body.

11. The method of claim 10, further comprising:
    engaging the flange on a beveled surface defined by the at least one protrusion; and
    flexing the flange on the beveled surface such that the at least one protrusion is able to be received within the aperture.

12. The method of claim 9, wherein the gear retainer further comprises a locking mechanism offset from the wedge and also extending from the arm, and wherein installing the gear retainer on the head further comprises:
    angularly aligning the heel and the arm with the opening;
    occluding the opening with the heel and the arm; and
    receiving the locking flange between the wedge and the locking mechanism, thereby preventing axial displacement of the drive gear within the first axial bore.

13. The method of claim 12, wherein the locking mechanism comprises a beveled surface and a locking surface, the method further comprising:
    flexing the locking mechanism as the beveled surface engages the neck at the opening;
    snapping the locking mechanism into place at the opening; and
    engaging an inner surface of the first axial bore with the locking surface, thereby preventing the gear retainer from removal from the opening.

14. The method of claim 9, further comprising ultrasonically-welding the gear retainer to the head.

15. The method of claim 9, wherein installing the gear retainer on the head further comprises receiving one or more retainer protrusions defined on an inner circumferential surface of the gear retainer into an arcuate groove defined about at least a portion of the outer circumferential surface of the head.

16. A gear retainer for securing a drive gear and a driven gear within a prophylaxis angle housing, comprising:
    an annular body having a longitudinal axis and defining an inner circumferential surface configured to extend about an outer circumferential surface of a head of the prophylaxis angle housing when installed;
    a heel disposed on the inner circumferential surface of the annular body and extending on the inner circumferential surface along the longitudinal axis and out of the annular body;
    an arm extending from the heel at an angle; and
    a wedge extending orthogonally from the arm.

17. The gear retainer of claim 16, further comprising a flange extending from the annular body and at least partially defining an aperture configured to receive at least one protrusion defined on the outer circumferential surface of the head when the gear retainer is installed on the head.

18. The gear retainer of claim 16, further comprising a locking mechanism offset from the wedge and also extending orthogonally from the arm, the locking mechanism comprising:
    a beveled surface configured to engage an opening defined in the prophylaxis angle housing and cause the locking mechanism to flex and snap into place at the opening; and
    a locking surface configured to engage an inner surface of the prophylaxis angle housing, thereby preventing the gear retainer from removal from the opening.

19. The gear retainer of claim 18, wherein the heel and the arm of the gear retainer are configured to cover the opening, and wherein the wedge and the locking mechanism are configured to receive therebetween a locking flange defined in the drive gear to prevent axial displacement thereof within the prophylaxis angle housing.

20. The gear retainer of claim 16, further comprising one or more retainer protrusions defined on the inner circumferential surface of the gear retainer, the one or more retainer protrusions being configured to be received into an arcuate groove defined about at least a portion of the outer circumferential surface of the head.

* * * * *